United States Patent [19]
Johnson et al.

[11] Patent Number: 5,460,185
[45] Date of Patent: Oct. 24, 1995

[54] TOOL AND METHOD FACILITATING RAPID PCTA CATHETER EXCHANGE

[75] Inventors: Kirk Johnson, Miami Lakes; Mark Inderbitzen, Miramar, both of Fla.

[73] Assignee: Cordis Corporation, Miami Lakes, Fla.

[21] Appl. No.: 218,071

[22] Filed: Mar. 25, 1994

[51] Int. Cl.$^6$ .................................................. A61B 5/00
[52] U.S. Cl. ................................................ 128/772; 604/96
[58] Field of Search .................................. 128/657, 658, 128/772; 604/95, 160, 280–283

[56] References Cited

U.S. PATENT DOCUMENTS

| | | | |
|---|---|---|---|
| 4,616,653 | 10/1986 | Samson et al. | 128/657 |
| 5,045,061 | 9/1991 | Seifert et al. | 128/772 |
| 5,163,911 | 11/1992 | Sirimanne et al. | 128/772 |
| 5,255,690 | 10/1993 | Keith et al. | 128/772 |
| 5,324,269 | 6/1994 | Miraki | 604/160 |
| 5,334,187 | 8/1994 | Fischell et al. | 604/160 |

*Primary Examiner*—Max Hindenburg
*Attorney, Agent, or Firm*—Watts, Hoffmann, Fisher & Heinke

[57] ABSTRACT

Apparatus for facilitating balloon catheter exchange in a vascular dilatation procedure using a balloon guidewire emplaced within the vascular system of a patient, and a balloon catheter defining an inflation lumen and a guidewire lumen and being attached at its proximal end to a hub. The apparatus includes a relatively short guidewire extension attached at its proximal end to a handle portion. The handle portion defines structure cooperative with the hub for facilitating sliding movement of the handle portion along the hub while the guidewire extension is at least partially inserted into the guidewire lumen. The handle portion is free to slide over the entire length of the hub and to slide off the hub in both proximal and distal directions. A guide element maintains the handle portion engaged for sliding movement along the balloon catheter. The guidewire lumen is slitted and the handle portion carries a separator for opening the slit in the region of the location of the handle portion. The guide element is separable from the handle portion and separates from the handle portion and docks at the distal end of the hub when the handle portion is slid past the hub's distal end in a proximal direction.

19 Claims, 6 Drawing Sheets

TOOL AND METHOD FACILITATING RAPID PCTA CATHETER EXCHANGE

TECHNICAL FIELD

This invention relates generally to the field of vascular dilatation procedures, such as angioplasty, and more particularly to an improved tool and method for facilitating rapid insertion of a balloon catheter onto an already emplaced balloon guidewire.

BACKGROUND ART

Cardiac catheterization procedures are well known for diagnosis and therapy relating to lesions in the cardiovascular system. One such procedure is angioplasty, for eliminating or ameliorating vascular plaque blockage or constriction in vessels which carry the heart's blood supply. In an angioplasty procedure, an expandable balloon is introduced into the patient's arterial system and advanced until it is positioned in the region of the blockage or constriction. Once so positioned, i.e., "emplaced", the balloon is expanded by filling it with a liquid. In successful procedures, the expandable balloon presses outwardly against the walls of the artery and expands the artery to a degree to which the artery is either partially or totally re-opened to blood flow.

A typical angioplasty procedure, and components used in practicing the procedure, are now described.

Prior to initiating the angioplasty procedure, a guiding catheter is placed, typically via the femoral artery, into the aorta and its tip is advanced to the entrance of the coronary arteries which branch from the aorta. This entrance into the coronary arteries is called the "ostium". Once placed, the guiding catheter acts as a conduit to access the coronary arteries with a balloon guidewire and balloon catheter. The guiding catheter is a portion of plastic tubing having a length of about 95 centimeters, an inside diameter of about 0.08 inches, and an outside diameter of about 2.5 millimeters.

The physician, in one known procedure, threads a balloon catheter onto a balloon guidewire. This operation takes place external to the patient.

The balloon guidewire is a piece of stainless steel and platinum wire, approximately 175 centimeters in length, and about 0.010–0.018 inches in diameter. The soft distal tip of the guidewire can be shaped to form a "J" configuration. This "J" shape allows the physician to steer the wire by twisting the proximal extremity of the wire while advancing or retracting the wire.

One type of balloon catheter is an elongated flexible plastic member defining two longitudinal passages and having a balloon located near its distal end. One longitudinal passage defines a closed tubular sleeve through which the balloon guidewire can be passed, and which completely surrounds the balloon guidewire over most of the catheter's length. The other longitudinal passage defines a conduit communicating with the interior of the balloon and through which inflation fluid can be injected to inflate the balloon. The passage defining the sleeve for accommodating a guidewire is often called the "guidewire lumen". The passage defining the conduit for inflation fluid is often called the "inflation lumen".

Balloon catheters having a closed tubular guidewire lumen enclosing the balloon guidewire over most of its length are called "over the wire" catheters.

Among the types of over the wire balloon catheters is one of a type in which the two longitudinal passages are generally side by side and parallel. In another type of over the wire balloon catheter, the two longitudinal passages are co-axial. In this latter type, the balloon guidewire is passed down the inner central passage and the inflation fluid is injected into the balloon via the outer passage.

Balloon catheters of another type, sometimes called "on the wire" catheters, as well as associated apparatus and method for use in angioplasty, are described in U.S. Pat. No. 5,040,548, issued on Aug. 20, 1991, to Yock, and U.S. Pat. No. 4,762,129, issued on Aug. 8, 1988. Each of these issued U.S. patents is hereby expressly incorporated by reference.

The physician, in using an over the wire balloon catheter, passes the balloon guidewire through the appropriate one of the longitudinal passages in the balloon catheter, leaving a portion of the balloon guidewire extending from the distal end of the balloon catheter and also a portion extending from its proximal end.

This assembly is then inserted into the proximal end of the guiding catheter, distal end first. The assembly is inserted until the balloon which is attached near the distal end of the balloon catheter is near the distal end of the guiding catheter. At this point, the physician, while maintaining the balloon catheter stationary, pushes on the balloon guidewire to advance it outwardly from the distal end of the guiding catheter.

The balloon guidewire can be steered by appropriate twisting movement by the physician.

The physician steers the balloon guidewire into the chosen one of the coronary arteries, and advances it until it reaches a location of constriction which the physician desires to re-open. Carefully, the physician eases the balloon guidewire through the region of restriction until a portion of the balloon guidewire is beyond the constriction, relative to the guiding catheter.

With the balloon guidewire held stationary, the physician then advances the balloon catheter. The distal end of the balloon catheter, as it is advanced, will, of course, follow the balloon guidewire which is already in place.

The physician continues to advance the balloon until it is located in the region of constriction of the artery. With the balloon and its associated catheter held stationary, inflation fluid is injected into the conduit which communicates with the balloon, causing it to inflate. Inflation of the balloon expands the walls of the artery in the region of constriction and, in successful procedures, re-opens the artery to sufficient blood flow.

Arteries vary in size, and therefore balloon catheters having balloons of different sizes are provided for the physician's selection. These balloons, when inflated, range from about 1.5 millimeters to about 4 millimeters in diameter.

Sometimes, it is necessary for the physician to use more than one balloon to open an artery. Sometimes, the chosen balloon is too large to be advanced into the constricted area. In other instances, the first chosen balloon size, even when inflated, is not large enough to open the constricted area to the degree desired. In such cases, it is necessary to exchange one balloon for another during the same angioplasty procedure.

In order to accomplish this exchange, the balloon guidewire is left in place, and the balloon catheter is withdrawn entirely from the guiding catheter until it is completely disengaged from the balloon guidewire. A new balloon catheter, having a different sized balloon, is then re-inserted over the balloon guidewire and advanced back to the location of the constricted area, where it is used to effect the desired result.

Once the balloon guidewire is initially in place, extending past the constricted area, it is highly desirable to leave the balloon guidewire in place for the entire remainder of the angioplasty procedure. This means that the balloon guidewire must remain in place even during exchanges of balloons. The reason for this is that, when a foreign object, such as the balloon guidewire, is introduced into an artery, the artery walls sometimes go into spasm, and constrict generally along a substantial portion of its length. If the artery tends to contract in this way, removal of the balloon guidewire while the artery is so contracted will sometimes render it virtually impossible to reinsert the guidewire through the contracted artery.

Withdrawal of the balloon catheter, while preventing movement of the balloon guidewire, is a difficult and cumbersome procedure. This procedure has required both a second individual, in addition to the physician, and the attachment of a removable extension to the proximal end of the guidewire.

In the catheter exchange procedure, removal of the catheter, and the insertion of the new catheter, is done manually. This is a two-hand operation for the physician. In addition, an attendant must hold the balloon guidewire longitudinally fixed with respect to the patient during the catheter exchange procedure.

Holding the balloon guidewire longitudinally fixed has been a difficult task. One reason for this is that, when the catheter to be removed is being slid proximally along the guidewire, friction between the balloon catheter and the balloon guidewire tends to dislodge the balloon guidewire and move it in the proximal direction. As pointed out above, it is undesirable that the balloon guidewire move longitudinally during the exchange operation.

When a new catheter is being threaded upon an indwelling balloon guidewire, frictional forces tend to be generated which urge the balloon guidewire toward longitudinal movement in the distal direction. This, too, is undesirable.

It is a general object of the present invention to provide apparatus for facilitating rapid catheter exchange in a vascular dilatation procedure.

DESCRIPTION OF THE INVENTION

The general objection of the present invention is implemented by an apparatus for facilitating rapid catheter exchange during a vascular dilatation procedure employing a balloon guidewire emplaced within the vascular system of the patient. The apparatus includes a balloon catheter defining both a guidewire lumen and an inflation lumen. The balloon catheter is attached, at its proximal end, to a hub. The hub defines an inflation port which communicates with the inflation lumen of the balloon catheter. The hub also defines a conduit which extends generally parallel to and aligned with the proximal end of the balloon catheter at the point at which it is attached to the hub. This conduit consists of a bore extending longitudinally through the entire hub and communicating at the distal end of the hub with the proximal end of the guidewire lumen. The hub also defines a slot extending longitudinally over the entire length of the conduit and communicating with the conduit, to enable access to the conduit from locations external to the hub and near the slot.

A handle assembly is provided. The handle assembly includes a short guidewire extension and a handle portion attached to the proximal end of the guidewire extension. The handle portion defines an ear suitable for manual grasping by a user. The handle portion also includes structure which cooperates with structure of the hub to enable the handle portion to slide freely along the entire length of the hub in the neighborhood of the slot. In fact, the handle can slide freely off either the proximal or the distal end of the hub.

A guide member is provided. The guide member has structure cooperative with the handle portion to separably link the guide member to the handle portion. The guide member links with the handle portion and engages the balloon catheter when the handle portion is slid distally off the distal end of the hub and onto the balloon catheter. The guide member provides a guiding force to facilitate the handle member generally tracking undulations in the balloon catheter as the handle portion and guide member are slid in unison along the balloon catheter.

During the time that the handle portion and guide member are sliding in either direction along the balloon catheter, the guidewire extension extends distally from the handle member and slides in unison with handle member movement. During this time, the guidewire extension resides within the guidewire lumen.

In order to facilitate the movement in unison of the guidewire extension and handle portion, while the handle portion is external to the guidewire lumen and the guidewire extension is internal to the guidewire lumen, the guidewire lumen is slitted over much of its length. The handle portion is provided with a blade which rides along with the handle portion and extends into the slit, forcing the slit open in the general region of the position of the handle portion. This opening of the slit in the region of the handle portion provides the access for the guidewire extension to extend from the external handle portion into the interior of the guidewire lumen.

The guide member is constructed to cooperate with the distal end of the hub such that, when the handle member, guidewire extension and guide member are moved in a proximal direction past the distal end of the hub, the guide member separates from the handle portion and becomes "docked" on the distal end of the hub as the handle portion and guidewire extension continue their proximal movement.

In use, a user, such as a physician, first emplaces a balloon guidewire within the patient's vascular system. He then threads the guidewire extension into the conduit and into the proximal end of the guidewire lumen of the balloon catheter. By applying manual force, the physician slides the handle portion, the guide member and the guidewire extension in a distal direction along the balloon catheter until the distal end of the guidewire extension protrudes from the distal end of the balloon catheter. The distal end of the guidewire extension is provided with mechanism for engaging the proximal end of the balloon guidewire. The physician then engages the guidewire extension onto the balloon guidewire. Holding the handle portion and guidewire extension, along with the balloon guidewire stationary, the user then threads the balloon catheter onto the balloon guidewire until the balloon catheter has reached a desired position within the patient's body.

The balloon catheter can be fed onto the balloon guidewire to such an extent that the hub, instead of being proximal to the handle portion and balloon guidewire becomes distal to the handle portion as the handle portion passes in a proximal direction relative to the hub, to a point at which the handle portion is actually proximal to the entirety of the hub itself. The handle portion, during this entire procedure, subsequent to the engagement of the guidewire extension with the balloon guidewire, has not moved. Only the balloon catheter has moved relative to the handle portion and the guidewire extension. This invention facilitates the one-handed holding stationary of the balloon guidewire within the patient's body, enabling the physician to use his other hand to advance or retract the balloon catheter, thus simplifying and improving the rapidity with which catheter exchange can be effected.

The invention will be better understood with reference to the following detailed description, and to the drawings, in which:

BEST MODE FOR PRACTICING THE INVENTION

Figures 1, 2:
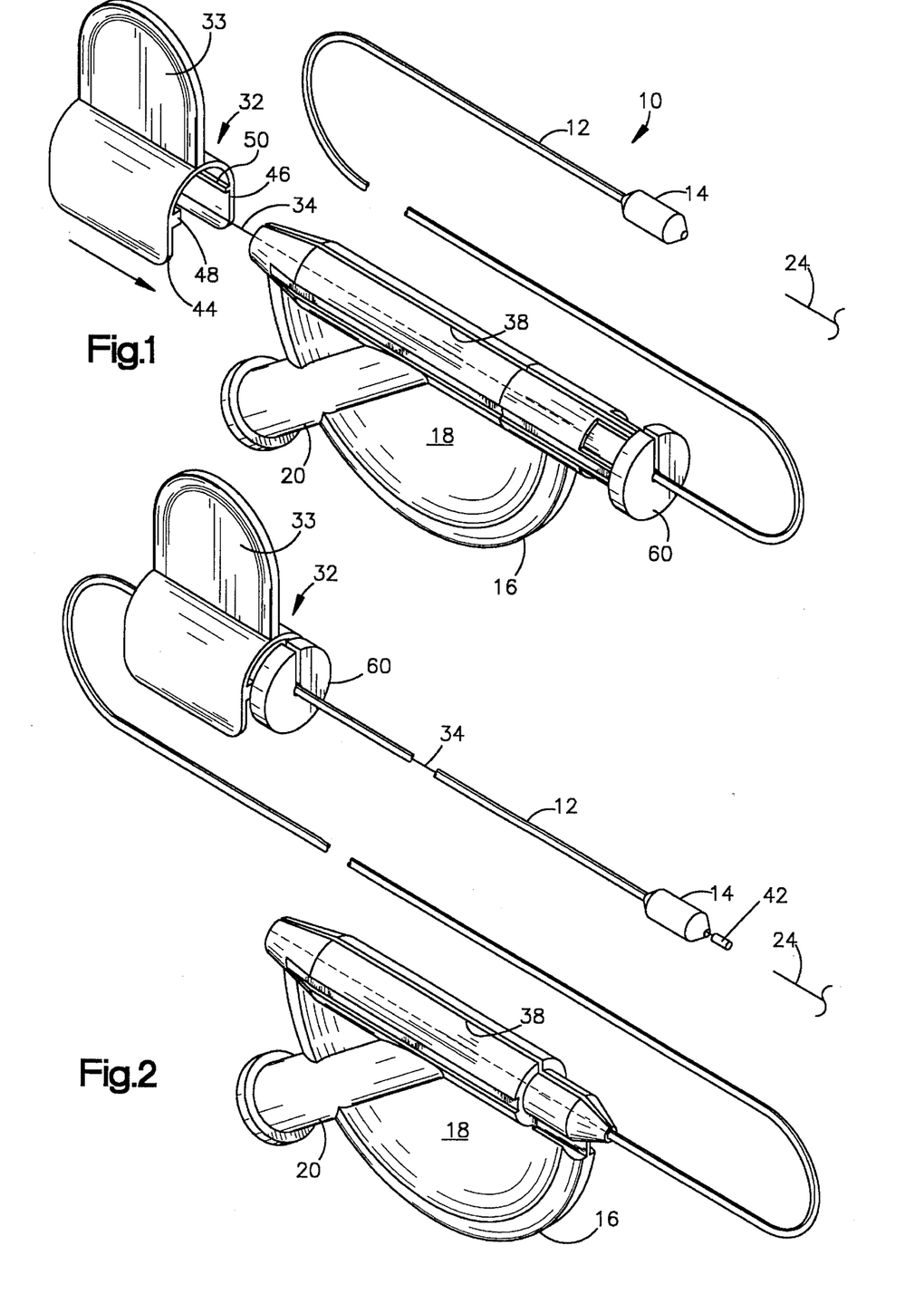
FIG. 1 illustrates the catheter exchange system of the present invention in a mode preparatory to use.
FIG. 2 illustrates the system of FIG. 1, in a configuration ready to begin use.

FIG. 1 illustrates a system 10 for facilitating rapid exchange of balloon catheters in vascular dilatation procedures such as angioplasty. FIG. 1 illustrates a balloon catheter 12. The balloon catheter 12 is tipped by a balloon 14, shown only in very general form in FIG. 1.

The proximal end of the balloon catheter is permanently affixed, such as by fusion, to a hub 16. The hub 16 includes a body portion 18 which defines an inflation port 20.

Figure 9:
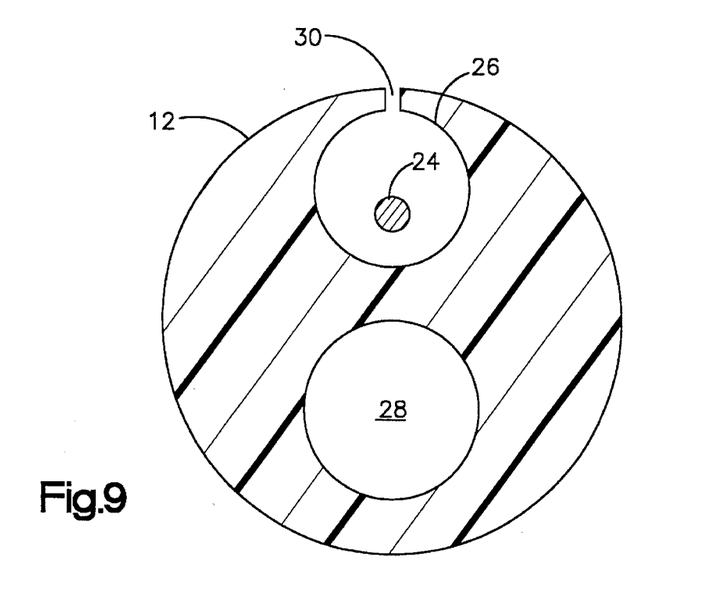
FIG. 9 is a cross-sectional view illustrating in detail the cross section of a balloon catheter of the system of FIG. 1.

The balloon catheter 12 is illustrated in cross section in FIG. 9. In this particular embodiment, the balloon catheter is of the so-called "dual lumen" construction, wherein the balloon catheter defines two longitudinally extended lumens, one for accommodating a balloon guidewire 24, which guidewire lumen is indicated by the reference character 26. Additionally, the balloon catheter defines an inflation lumen 28. The inflation lumen 28 extends longitudinally through the balloon catheter in a generally parallel, side-by-side relationship with guidewire lumen 26. The inflation lumen 28 communicates between the inflation port and the interior of the balloon 14.

The guidewire lumen 26 is slitted. The slit is shown in FIG. 9 and designated by reference character 30. The slit extends from the proximal end of the guidewire lumen all the way to within about 27 centimeters of the distal end of the balloon catheter, at which point the slit terminates and the remainder of the distal portion of the balloon catheter is unslitted.

The system also includes a handle assembly 32. The handle assembly 32 includes a handle portion 33 which holds a short guidewire extension 34 for engagement with the proximal end of the balloon guidewire 24 when the guidewire 24 is emplaced within the patient's vascular system. The short guidewire extension 34 is about 30 centimeters in length. The proximal end of the guidewire extension 34 is fixed within the interior of the handle portion 33 at a location designated in FIG. 7 by reference character 36.

Figure 8:
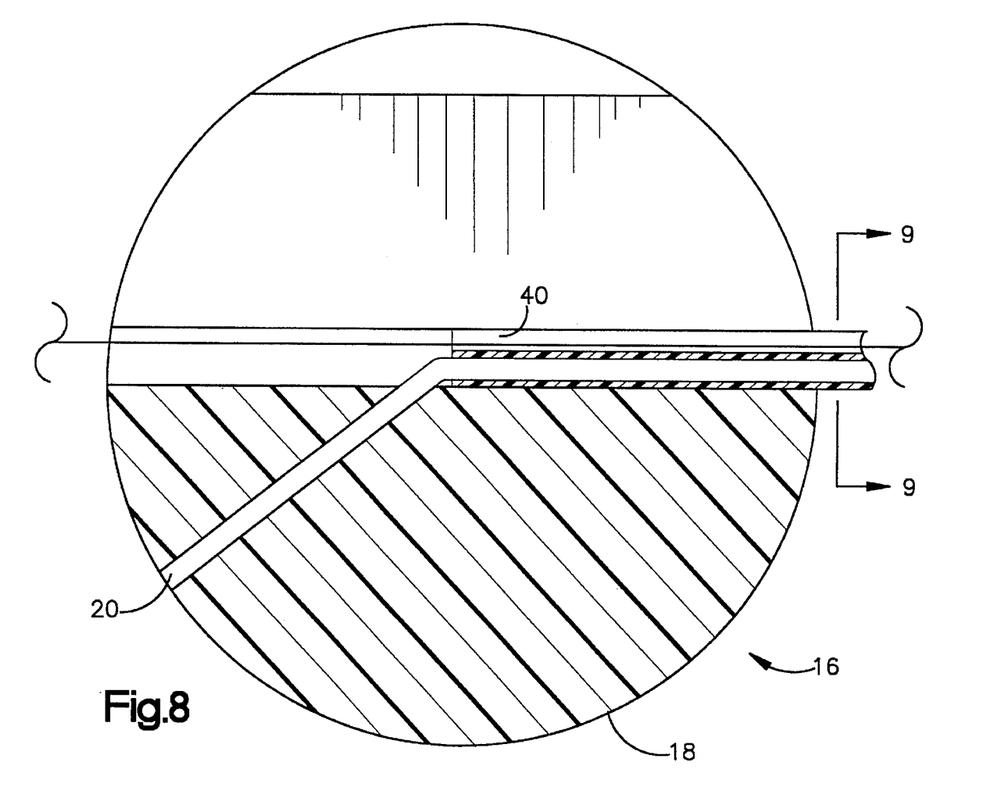
FIG. 8 is a cross-sectional view illustrating an enlarged detail portion of the portion of the system shown in FIG. 7.

The hub 16 defines a slot 38 extending longitudinally along the top of the hub. The slot 38 communicates with an interior bore 40, as shown in FIG. 8. The bore 40 extends longitudinally through the entirety of the hub 16. The slot 38 and the bore 40 are suitably sized to accommodate therewithin the short guidewire extension 34 which is attached to the handle portion 33.

Figures 10, 11, 12:
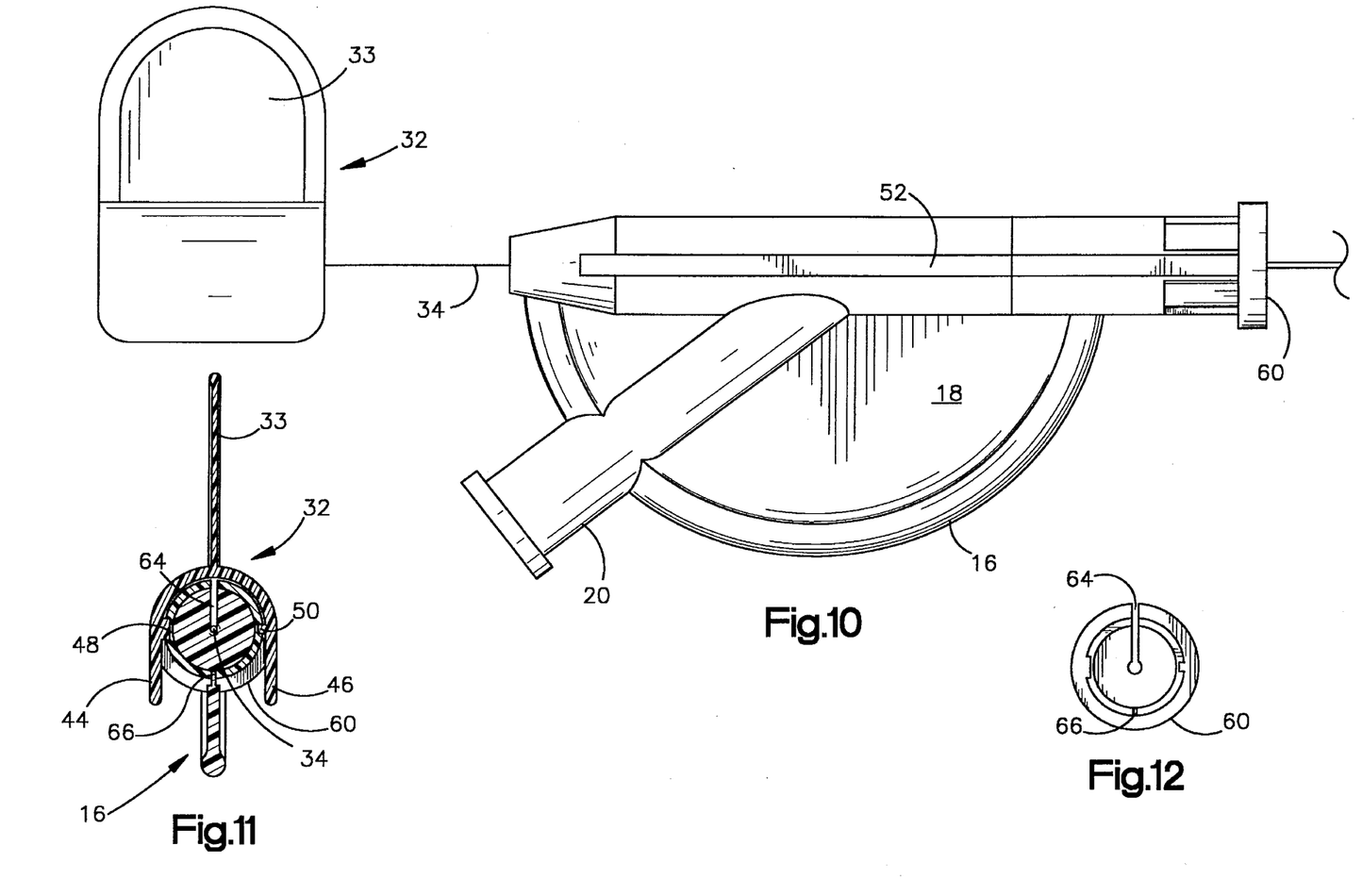
FIG. 10 illustrates a handle portion and guidewire extension which is a part of the apparatus illustrated in FIGS. 1–6E.
FIG. 11 is a sectional view of a handle assembly, a guiding cylinder and a hub as seen from a plane indicated by 11—11 in FIG. 3.
FIG. 12 is an end view of the guiding cylinder.

FIG. 10 illustrates the handle assembly 32 comprising the handle portion 33 and the guidewire extension 34. The guidewire extension 34 is tipped at its distal end with a mechanism generally designated at 42, for engaging and holding the proximal end of the balloon guidewire 24. The engagement mechanism 42 is of a type described in U.S. Pat. No. 5,113,872, issued May 19, 1992 and owned by the assignee of the present application. This patent is hereby expressly incorporated by reference.

The handle portion 33 includes an ear suitable for manual grasping by a physician using the system, and two attached legs 44, 46. The legs 44, 46 are sized to snugly accommodate between them the top portion of the hub 16, which top portion has a generally cylindrical configuration. Thus, the handle portion 33 is designed for engaging and sliding along the top portion of the hub 16, in a longitudinal direction parallel to that of the slot 38.

Extending longitudinally on the inside of each of the legs 44, 46 are rails 48, 50, respectively. The rails 48, 50 are sized for sliding engagement within respective corresponding longitudinally extending channels in the sides of the upper portion of the hub 16. One of the longitudinally extending channels is designated by reference character 52 in FIG. 1. The other channel is substantially opposite channel 52, but, for purposes of simplicity, is not illustrated in the drawings.

Figure 6C:
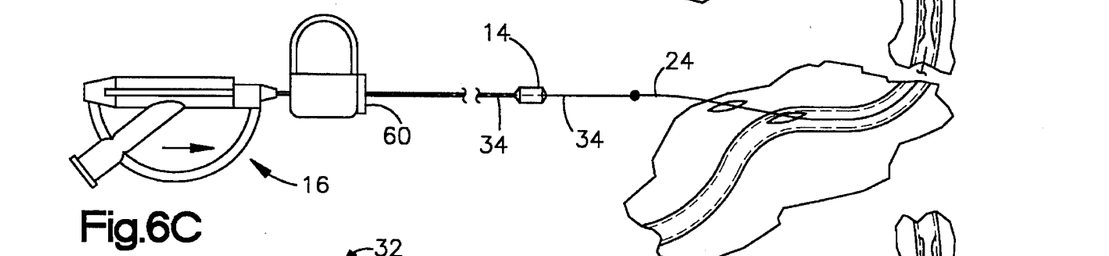
Figure 7:
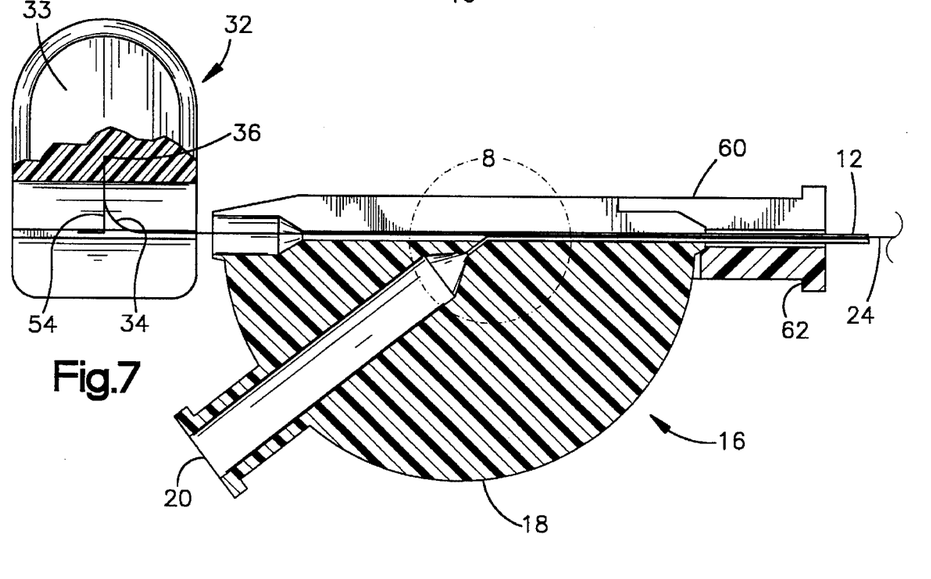
FIG. 7 is a cross-sectional view illustrating a portion of the system of FIGS. 1–5.

The handle portion 33 includes a separator 54 (FIG. 7). The separator 54 which can be, for example, a T-shaped wire, extends downwardly between the legs of the handle portion 33. The separator 54 is positioned to open the slit of the balloon catheter 12 as the balloon catheter is (that is, moved to the right with respect to the handle assembly 32 as shown in FIG. 6C). When the handle assembly 32 is moved distally with respect to the balloon catheter 12, an upper portion of the extension wire 34 functions to open the slit 30 of the balloon catheter. The handle relative motion between the handle portion 33 and the balloon catheter 12 will be described in more detail below.

It can be seen that the handle portion 33, by virtue of engagement of the rails with the channels, can slide longitudinally along the length of the hub. The handle portion 33 can slide freely off either end of the hub.

As will be explained in more detail below, it is necessary for the handle portion 33, to which is attached the short guidewire extension, to be able to slide freely along the length of the balloon catheter without coming loose from the balloon catheter. The balloon catheter provides guidance for the sliding motion of the handle portion 33 and short guidewire extension.

A guiding cylinder 60 (FIG. 12) is provided to constrain the handle portion 33 to follow the bends of the balloon catheter as the handle portion 33 is slid along the balloon catheter. The guiding cylinder 60 is a single-piece article, separate from the hub 16 having a stepped head portion 62 which is near the righthand end of the guiding cylinder, as it appears in, for example, FIG. 7.

The guiding cylinder 60 defines two longitudinal slots in its outer surface. These include a full-length slot 64, extending through the outer wall of the cylinder 60, longitudinally, for the entire length of the cylinder. A partial slot 66 is also defined in the cylinder wall. The partial slot 66 is diametrically opposed to the location of the full-length slot 64.

In use, when the handle portion 33 is sliding along the balloon catheter, the guiding cylinder 60 is attached to the proximal end of the handle portion 33. The guiding cylinder 60 is sized to fit snugly within the legs defined by the handle portion 33, and to be held within those legs. The length of the guiding cylinder is approximately equal to the length of the handle legs. Thus, the handle legs straddle the guiding cylinder. In this use configuration, with the handle portion 33 sliding along the balloon catheter, the guiding cylinder is positioned such that its partial slot faces downwardly between the legs of the handle portion 33, while the full-length slot 64 faces upwardly and abuts the underside of the handle portion, between the closed ends of the legs.

It is notable that, as the handle portion 33 slides along the balloon catheter, the separator 54 continuously rides along and separates the slit defined in the guidewire lumen of the balloon catheter. This separation of the slit facilitates the short guidewire extension being placed within the guidewire lumen. Bear in mind that, in this configuration, the balloon guidewire is already emplaced within the patient, and, at this time, the balloon guidewire is not present within the guidewire lumen of the balloon catheter.

In this configuration, the short guidewire extension, which is attached to the handle portion 33, rides within the empty guidewire lumen of the balloon catheter. Manual movement of the handle portion, while holding the balloon catheter substantially stationary, results in the handle sliding along the balloon catheter and the short guidewire extension sliding within the guidewire lumen in unison with handle movement.

The function of the guiding cylinder 60, which also rides along with the handle portion 33, is to maintain the balloon catheter within the space defined by the handle legs. The balloon catheter extends through a central opening in the guiding catheter defined by the full-length slot 64.

Details of the guiding cylinder are described in FIGS. 11 and 12.

Use of the catheter exchange system of the present invention is illustrated in the sequence of FIGS. 1–5.

Figure 6A:
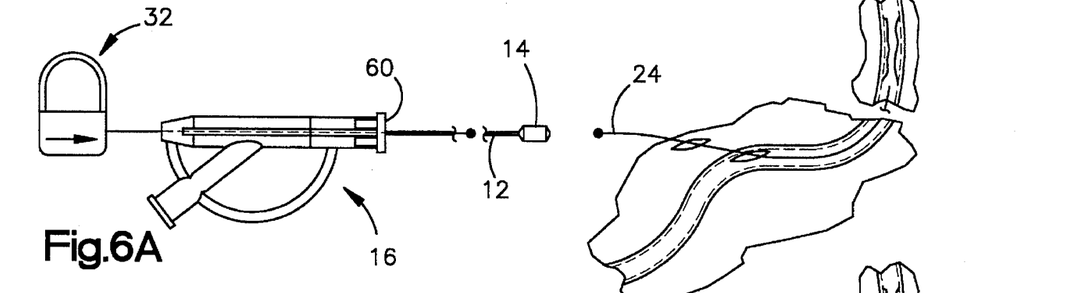
FIGS. 6A–6E are schematic drawings depicting the apparatus of the present invention in various aspects of its operation.

FIGS. 1 and 6A illustrate the system in a configuration preparatory to use. The handle portion 33 is located proximally with respect to the hub 16. The short guidewire extension 34 extends down the center of the cylindrical portion of the hub. As mentioned above, the short guidewire extension is about 30 centimeters in length. The short guidewire extension 34, upon passage to the right through the cylindrical portion of the hub, enters the proximal end of the guidewire lumen of the balloon catheter. In this position, the guiding cylinder is docked on the distal end of the hub 16. Note that, in FIG. 1, the balloon guidewire 24 has already been emplaced within the patient's vascular system, and extends outwardly a short distance from the point of entry.

Figure 6B:
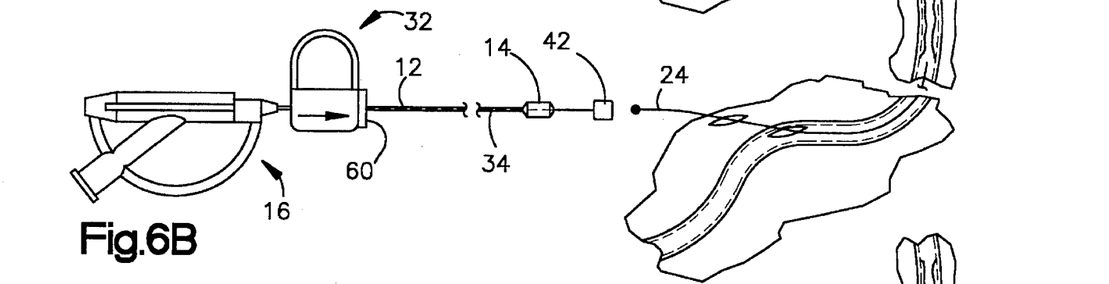

As the system is illustrated in FIGS. 2 and 6B, the handle portion 33 has been advanced distally over the cylindrical portion of the hub and has picked up the guide cylinder 60, which rides along the balloon catheter slightly ahead of the handle portion 33. A user, such as a physician, has manually advanced the handle portion 33, along with the guide cylinder 60, until the distal end of the short guidewire extension 34 can be seen protruding from the distal end of the guidewire lumen of the balloon catheter.

Subsequently, the user engages the distal end of the short guidewire extension 34 to the proximal end of the balloon guidewire by the use of the engagement mechanism 42 described above. Then, with the user maintaining the guidewire stationary by grasping the ear of the handle portion 33 and holding the handle portion 33 stationary, the user can, with his or her other hand, advance the balloon catheter along the guidewire extension, and then along the balloon guidewire until the balloon of the balloon catheter is in the appropriate position for therapeutic use.

Figure 3:
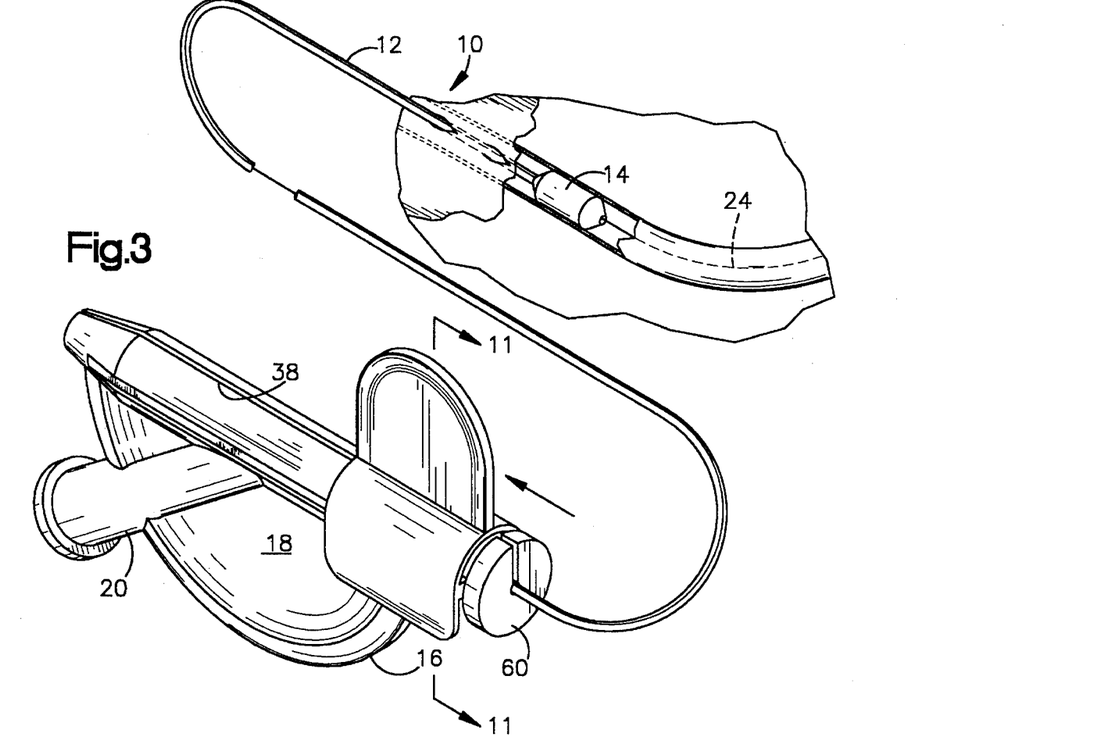
FIGS. 3, 4 and 5 illustrate the system of FIG. 1 during various aspects of use.
Figure 6D:
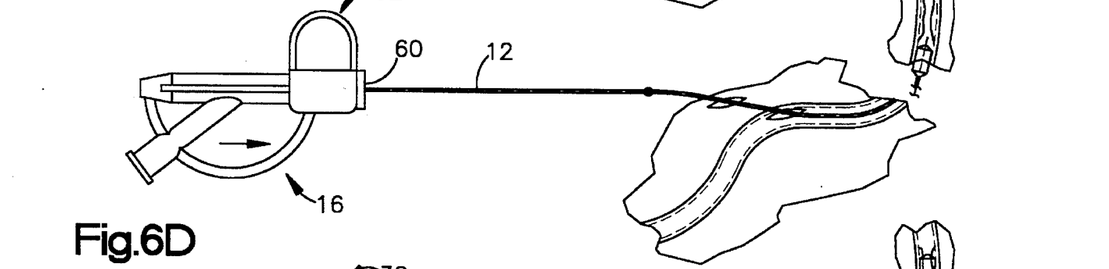

The user can advance the balloon catheter distally onto the balloon guidewire for a distance sufficient such that the hub 16 actually reaches the handle portion 33. At this point, as illustrated in FIGS. 3 and 6D, the proximal end of the handle portion 33 engages the distal end of the hub 16.

If even further advancement of the balloon catheter is desired, the hub can actually move distally to pass by the handle portion 33. When this occurs, the guide cylinder 60 engages, or becomes "docked" with the distal end of the hub, and the handle portion 33 separates from the guide cylinder as the hub moves to the right as, for example, shown in FIGS. 4 and 6E. The FIGS. 4 and 6E configurations show the handle portion having passed proximally over the hub, being located proximally separate from the hub.

Figure 4:
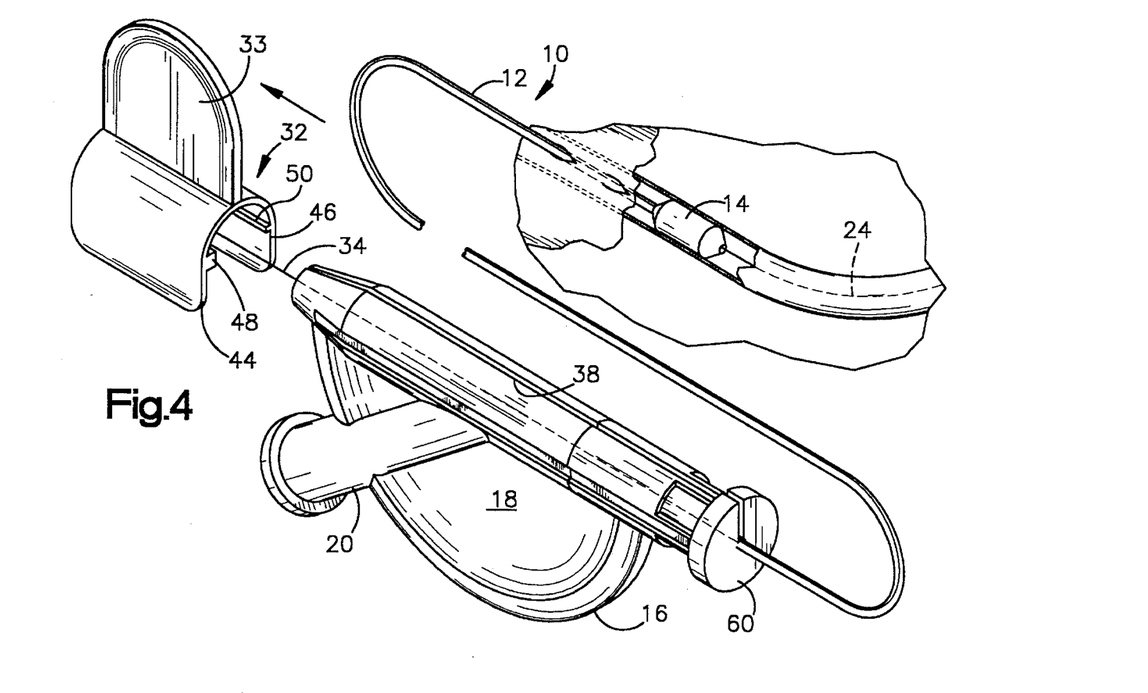
Figure 6E:
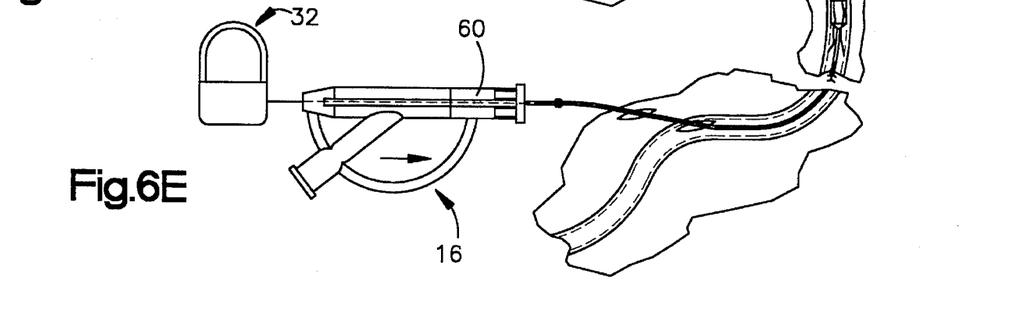

All the while, the handle portion 33 is held stationary, holding the balloon guidewire and the short guidewire extension stationary as well, while the balloon catheter is manipulated in a distal direction.

Figure 5:
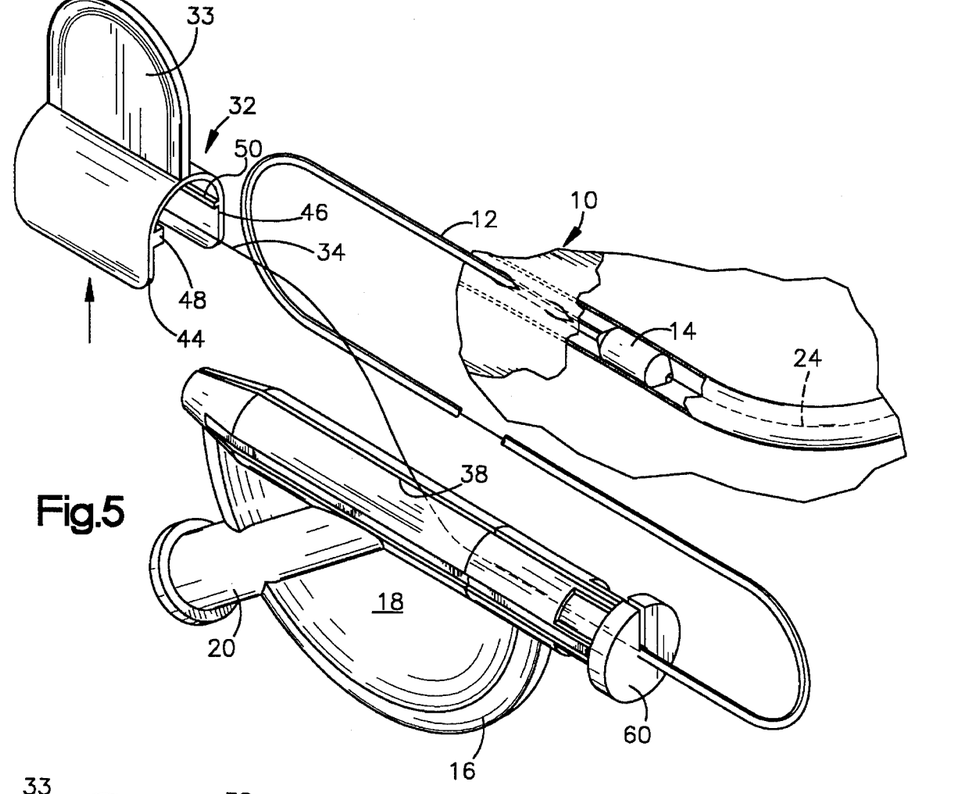

FIG. 5 illustrates the system of the present invention during stripping of the short guidewire extension from within the guidewire lumen of the balloon catheter. The guidewire extension 34 is stripped out of the guidewire lumen by raising the handle portion 33 and working the guidewire extension out of the longitudinal slot 38 which extends along the full length of the hub 16. If this is continued, and the guidewire extension 34 continues to engage the proximal end of the balloon guidewire, the balloon guidewire can be stripped out of the guidewire lumen in a similar manner. Also, where it is desired to withdraw the catheter from the patient, the user continues to hold stationary the handle portion 33, and, with the other hand, exert tension on the balloon catheter in a proximal direction, which causes the catheter to slide over the balloon guidewire and outwardly from the patient. As the catheter emerges, the hub 16 can be moved downwardly, causing the balloon catheter to be stripped away from the guidewire extension.

While a specific embodiment of the present invention has been described with some particularity, it is to be understood that those of ordinary skill in the art may be able to make certain additions or modifications to, or deletions from, the specifics of the described embodiment, without departing from the spirit or the scope of the claims, as set forth below.

We claim:

1. An apparatus for facilitating catheter exchange in a vascular dilatation procedure employing a balloon guidewire emplaced in a patient's vascular system, said apparatus comprising:

a) a balloon catheter defining a guidewire lumen and an inflation lumen;

b) a hub attached to the proximal end of said balloon catheter and defining an inflation port communicating with said inflation lumen and a conduit communicating with said guidewire lumen; and c) a handle assembly comprising:
   i) a guidewire extension; and
   ii) a handle portion attached to the proximal end of said guidewire extension, said hub and said handle portion defining cooperating structure facilitating sliding movement of said handle portion over the entire length of said hub from a location proximal to said hub to a location distal to said hub, said hub further defining structure facilitating placement of said guidewire extension for sliding movement within said conduit in unison with sliding movement of said handle portion along said hub.

2. The apparatus of claim 1, further comprising:

a guide element having structure facilitating separable linkage with said handle portion for maintaining said handle portion in sliding engagement with said balloon catheter when said handle portion is distal to said hub.

3. The apparatus of claim 2, wherein:

said guide element and said hub define cooperative structure for causing said guide element to dock on the distal end of said hub and to separate from said handle portion when said handle portion is moved proximally past the distal end of said hub.

4. The apparatus of claim 1, wherein:

a) said guidewire lumen is slitted for a portion of its length; and b) said handle portion comprises a separator positioned for opening said slit of said guidewire lumen in the region of said handle portion when said handle portion is positioned at a location along said balloon catheter.

5. A handle assembly for use in facilitating balloon catheter exchange in a vascular dilatation procedure employing a balloon guidewire emplaced within a patient's vascular system and a balloon catheter defining an inflation lumen and a guidewire lumen, the balloon catheter being attached at its proximal end to a hub defining an inflation port communicating with said inflation lumen and a conduit communicating with said guidewire lumen, said handle assembly comprising:

a) a guidewire extension;

b) a handle portion attached to the proximal end of said guidewire extension and having an ear facilitating manual grasping of said handle portion, said handle portion having structure cooperating with said hub for facilitating sliding movement of said handle portion along said hub while said guidewire extension is located within said conduit; and c) mechanism for engaging the distal end of said guidewire extension with the proximal end of said balloon guidewire.

6. A method for use in connection with vascular dilatation procedures in a patient, utilizing a balloon guidewire, a balloon catheter defining a guidewire lumen and being attached to a hub, and a handle assembly including a handle portion attached to a guidewire extension bearing an engagement mechanism at its distal end, said method comprising the steps of:

a) emplacing the balloon guidewire in a patient's vascular system;

b) threading the distal end of the guidewire extension through the hub into the guidewire lumen of the catheter;

c) advancing the handle and the guidewire extension distally along the catheter until the distal end of the guidewire extension protrudes from the distal end of the guidewire lumen of the catheter;

d) engaging the proximal end of the guidewire with the distal end of the guidewire extension by use of said engagement mechanism;

e) while holding the guidewire substantially stationary by use of the handle portion, advancing the catheter guidewire lumen distally onto the guidewire and into the patient's vascular system;

f) continuing to advance the catheter by advancing the hub distally relative to the handle; and g) continuing to advance the catheter by advancing the hub distally with respect to the handle portion until the handle portion is located proximal to the hub.

7. A method for use in connection with vascular dilatation procedures in a patient, utilizing a balloon guidewire, a balloon catheter defining a guidewire lumen and being attached to a hub, and a handle assembly including a handle portion attached to a guidewire extension bearing an engagement mechanism at its distal end, said method comprising the steps of:

a) emplacing the balloon guidewire in a patient's vascular system;

b) threading the distal end of the guidewire extension through the hub into the guidewire lumen of the catheter;

c) advancing the handle and the guidewire extension distally along the catheter until the distal end of the guidewire extension protrudes from the distal end of the guidewire lumen of the catheter;

d) engaging the proximal end of the guidewire with the distal end of the guidewire extension by use of said engagement mechanism; and e) while holding the guidewire substantially stationary by use of the handle portion, advancing the catheter guidewire lumen distally onto the guidewire and into the patient's vascular system.

8. An apparatus for facilitating advancement of a balloon catheter over a balloon guidewire, the balloon catheter having a hub coupled to its proximal end and including a guidewire lumen extending longitudinally within said catheter, the guidewire lumen sized to accept said guidewire; said catheter having a catheter slit from an outer surface of the catheter to the guidewire lumen, the slit extending longitudinally from the proximal end of the catheter over at least a portion of a length of the catheter, the hub having a central longitudinal opening aligned with the guidewire lumen and a longitudinal slot providing access to the central longitudinal opening, the longitudinal slot of the hub aligned with the catheter slit, the apparatus comprising:

a) a handle assembly including a guidewire extension sized for movement within the guidewire lumen and having an attachment mechanism near a distal end of the extension for engaging an end of the balloon guidewire, the handle assembly further including structure cooperative with a portion of the hub facilitating longitudinal sliding movement of the handle assembly relative to said hub; and b) a guiding member releasably attached to a distal end of the hub, the guiding member adapted to releasably engage the handle assembly when the handle assembly is advanced distally beyond a distal end of the hub and to guide the handle assembly along the catheter as the handle assembly is moved relative to the catheter such that the guidewire extension moves within the guidewire lumen.

9. The apparatus of claim 8, wherein said handle assembly structure cooperative with said hub comprises rail and channel slide mechanism.

10. The apparatus of claim 8, wherein said longitudinal slot of said hub is sized to facilitate passage therethrough of said guidewire extension and said central opening of said hub is sized to facilitate movement of the guidewire extension within said central opening.

11. The apparatus of claim 8, wherein said guiding member is substantially cylindrical in shape.

12. The apparatus of claim 8, wherein said guiding member defines a central core sized for accommodating passage therethrough of said balloon catheter.

13. The apparatus of claim 12, wherein said guiding member defines a first longitudinal slot communicating with said core and extending the entire length of said guiding member, said first longitudinal slot being sized to accommodate passage therethrough of said guidewire extension, and said guiding member also including structure for releasably attaching the proximal end of the guiding member to the distal end of the hub while fixing said first longitudinal slot of said guiding member aligned with said longitudinal slot of said hub.

14. The apparatus of claim 13, further comprising:

said guiding member defining a second longitudinal slot extending less than the entire length of said guiding member and means for releasably attaching said guiding member proximal end against a distal portion of the hub with said second longitudinal slot fixedly aligned with said longitudinal slot of said hub.

15. The apparatus of claim 8, wherein a structure for releasably engaging said guiding member to said handle assembly comprises a snap mechanism.

16. The apparatus of claim 8, wherein a structure for releasably engaging said guiding member to said handle assembly comprises a friction engagement structure.

17. The apparatus of claim 8, wherein a structure for releasably attaching said guiding member to said hub comprises a friction engagement structure.

18. The apparatus of claim 8, wherein a structure for releasably attaching said guiding member to said hub comprises a snap structure.

19. The apparatus of claim 8 wherein the handle assembly includes a separator member sized to extend into the catheter guidewire lumen and facilitate spreading open the catheter slit when the catheter is moved in a distal direction relative to the handle assembly.

* * * * *